US 6,511,372 B2

United States Patent
Leeds et al.

(10) Patent No.: US 6,511,372 B2
(45) Date of Patent: Jan. 28, 2003

(54) APPARATUS FOR CONTROLLING GAS FLOW IN THERMODYNAMIC ENVIRONMENTAL TESTING DEVICES

(75) Inventors: Richard L. Leeds, St. Louis, MO (US); John D. Martin, Fountain Hills, AZ (US)

(73) Assignee: Controlled Environments, Inc., St. Louis, MO (US)

(*) Notice: Subject to any disclaimer, the term of this patent is extended or adjusted under 35 U.S.C. 154(b) by 0 days.

(21) Appl. No.: 09/800,241

(22) Filed: Mar. 6, 2001

(65) Prior Publication Data
US 2002/0127965 A1 Sep. 12, 2002

(51) Int. Cl.[7] .................................................. F24F 11/04
(52) U.S. Cl. ........................ 454/186; 138/46; 454/306
(58) Field of Search .............................. 454/185, 186, 454/284, 306, 305; 138/40, 45, 46

(56) References Cited
U.S. PATENT DOCUMENTS

| | | | |
|---|---|---|---|
| 1,527,222 A | 2/1925 | Rasmussen | |
| 2,197,614 A | * 4/1940 | Hall et al. | |
| 2,302,097 A | * 11/1942 | Beckman | |
| 2,635,006 A | 4/1953 | Richmond | |
| 3,258,848 A | 7/1966 | Watlington | |
| 5,099,587 A | * 3/1992 | Jarosch | |
| 5,147,136 A | 9/1992 | Hartley et al. | |
| 5,551,169 A | 9/1996 | Baker et al. | |
| 5,646,358 A | 7/1997 | Tikhtman et al. | |
| 6,023,985 A | 2/2000 | Fournier | |

FOREIGN PATENT DOCUMENTS

| | | | | |
|---|---|---|---|---|
| CH | 266894 | * | 1/1934 | |
| GB | 506443 | * | 5/1939 | ............ 454/306 |
| JP | 4-80548 | * | 3/1992 | ............ 454/289 |

* cited by examiner

*Primary Examiner*—Harold Joyce
(74) *Attorney, Agent, or Firm*—Thompson Coburn LLP

(57) ABSTRACT

A gas flow regulator comprises a gas passage duct that can be axially repositioned and rotationally reoriented relative to a chamber wall for controlling the flow rate of gas from one side of the wall into an interior volume on an opposite side of the wall.

17 Claims, 3 Drawing Sheets

APPARATUS FOR CONTROLLING GAS FLOW IN THERMODYNAMIC ENVIRONMENTAL TESTING DEVICES

BACKGROUND OF THE INVENTION

(1) Field of the Invention

This invention pertains to the field of gas flow regulators in thermodynamic environmental testing devices. More particularly, this invention pertains to a gas flow regulator comprising a gas passage duct that can be axially repositioned and rotationally reoriented relative to a chamber wall for controlling the flow rate of gas into the interior volume of a thermodynamic environmental testing chamber for increasing the spatial uniformity of the rate of temperature change throughout test specimens tested in the chamber. The flow regulator of the invention provides a simplistic and cost effective means of regulating the gas flow rate though a test chamber wall by merely axially and rotationally reorienting a gas passage duct relative to the cavity wall.

(2) Description of the Related Art

Thermodynamic environmental testing devices are used in various industries, primarily for testing the fatigue properties of test specimens, and operate by cycling the temperature of such test specimens. Testing devices typically comprise a large thermodynamically insulated box-like unit having one or more doors that provide access to an internal testing chamber therein. Heating and cooling of test specimens placed within the testing chamber is achieved by supplying heated or cooled gas into the chamber through ports communicating with the chamber interior volume. Using liquid nitrogen for cooling and electric heating elements for heat, the temperature change rates of test specimens can exceed 70° Celsius per minute.

During operation, the temperature of gas flowing into the testing chamber of a testing device is commonly controlled by an electronic control module. Among other things, such control modules typically allow control of the temperature change rates, the maximum and minimum testing chamber temperature, and the maximum and minimum temperature of gas being supplied into the testing chamber. This is done by programming the control module with specific temperature cycling parameters and by providing the control module with feedback of monitored testing chamber temperatures. Such control modules are also typically interfaced with heating, cooling, and blower systems for controlling such systems in an effort to achieve the programmed cycling parameters.

The heated or cooled gas is typically delivered into the testing chamber via a plenum having one or more ports communicating with the chamber interior. The ports often comprise flexible hosing which allow the heated or cooled gas to be delivered to various locations within the testing chamber to improve the performance and efficiency of the testing device.

Despite the ability to regulate the gas temperature and its overall flow rate into the testing chamber using prior art testing devices, it is difficult to achieve spatially uniform rates of temperature change throughout various test specimens or throughout portions of each test specimen. This is because various test specimens generally have various heat-sink properties and even a single test specimen can have different portions that require more or less total heat or cooling to achieve the same rate of temperature change as other portions thereof. Although directing the gas flow from each of the ports using flexible hoses helps reduce spatial variations of the rate of temperature change throughout the test specimens, the spatial variations of the rate of temperature change within the testing chambers of prior art testing devices is still problematic.

The present invention overcomes the disadvantages associated with prior art thermodynamic environmental testing devices by providing gas flow regulators capable of independently adjusting the gas flow rate of heating or cooling gas flowing through a plurality of supply ports from one or more plenums into a testing chamber. By allowing independent adjustment of the gas flow through the plurality of ports, the total amount of heating or cooling gas flowing into the testing chamber can be distributed in a manner that reduces spatial variations of temperature change rates throughout one or more test specimens. Furthermore, a unique gas flow regulator is employed that comprises a minimal number of components and that is capable of adjusting gas flow through a test chamber wall by merely adjusting its position and orientation relative to a portion of the cavity wall.

SUMMARY OF THE INVENTION

In its intended operative environment, the gas flow regulator of the invention is employed with a thermodynamic environmental testing chamber of the type described earlier. Apart from the presence of the novel gas flow regulator of the invention, the thermodynamic environmental testing chamber is constructed as any typical testing chamber.

The chamber has an exterior housing with an interior volume employed in testing specimens that are enclosed in the housing of the chamber. The housing includes one or more doors that provide access to the interior volume of the chamber. In addition, a plenum is provided inside the chamber housing. The plenum extends around opposite sides of the interior volume of the chamber and is supplied with a flow of gas from a source of the type described earlier. The gas flow through the plenum is either cooled or heated as desired for the particular test being conducted in the chamber. The plenum encloses a second, interior volume through which the gas flow passes. The second interior volume is enclosed by at least a first wall and a second wall of the plenum. The first wall of the plenum is provided with the supply ports that communicate the second volume of the plenum interior with the first volume of the chamber interior containing the test specimens.

As set forth above, the gas flow regulator of the invention is used in the typical thermodynamic environmental testing chamber described above in its preferred operative environment. However, it should be apparent that the simplistic construction and operation of the gas flow regulator of the invention may be employed in other similar environments where it is desired to provide a low cost and simple to operate regulator that adjusts the flow of gas from one volume on one side of a wall to another volume on an opposite side of the wall. To explain the construction and the operation of the gas flow regulator of the invention, the illustrative embodiment of the thermodynamic environmental testing chamber will be employed.

In the illustrative embodiment of the gas flow regulators, the gas flow supply ports in the plenum first wall separating the first volume of the test chamber interior from the second volume of the plenum interior are circular. The simplistic construction of each gas flow regulator is comprised of a cylindrical duct and a locking mechanism. The cylindrical duct has a selected length with opposite first and second ends. A cylindrical interior surface of the duct defines a passageway through the duct having a center axis. The exterior surface of the duct is cylindrical and has a circumferential dimension that matches the interior circumferential dimension of the holes of the ports in the first wall of the plenum so that the duct may be inserted into one of the holes in a tight friction fit. This enables the duct to slide within the hole while the edge of the plenum first wall around the hole provides support for the duct. The first end of the duct has an annular edge that lies in a plane perpendicular to the duct center axis. The opposite second end of the duct is beveled in shape. Preferably, the second end of the duct has an elliptically shaped edge that lies in a plane that is oriented obliquely to the duct center axis.

The gas flow regulator is assembled to the test chamber by the duct being inserted through one of the holes in the first wall of the plenum. The duct is positioned in the hole with the first end of the duct positioned in the first volume of the test chamber interior and the second end of the duct positioned in the second volume of the plenum interior. A gas flow regulator is assembled into each of the holes of the plenum ports.

The locking mechanism of the gas flow regulator is preferably an adjustable band clamp of the type known in the prior art. As in the typical band clamp, the band clamp of the regulator has opposite ends with slots formed across one end that function as rack teeth and a screw housing containing an adjustment screw at the opposite second end. The band first end is inserted through the screw housing forming the band in a loop, and on rotation of the screw in the screw housing the threads of the screw pass through slots of the band first end adjusting the size of the loop formed by the band.

The band of the locking mechanism is positioned over the exterior surface of the duct in the first volume of the test chamber interior where it is accessible from the test chamber. The screw housing of the locking mechanism is secured to the plenum first wall to hold the locking mechanism stationery relative to the first wall. By screwing the screw in the screw housing of the locking mechanism, the band is constricted around the duct and thereby holds the duct in a stationary position relative to the first wall of the plenum.

In the illustrative environment of the invention, a gas flow regulator is positioned in each hole in the air plenum first wall to regulate the flow of gas through the second volume of the plenum interior to the first volume of the test chamber interior.

In operation of the test chamber employing the flow regulator of the invention, the test chamber is activated causing a flow of gas (either heated or cooled) through the second volume of the plenum interior. It is typical that the flow of gas be directed in a single direction from the source of the gas flow toward the holes in the first wall of the plenum. The duct of the gas flow regulator positioned in each of the first wall holes channels the gas from the interior volume of the plenum through the passageway of the duct, and into the interior volume of the test chamber.

With the duct second end in the interior volume of the plenum having a beveled edge, rotating the duct in the plenum wall hole so that the elliptical opening of the beveled edge faces into the flow of gas through the plenum will result in a greater amount of the gas flow being channeled through the passageway of the duct and into the test chamber interior. Turning the duct 180 degrees in the plenum wall hole so the elliptical opening of the beveled edge faces away from the flow of gas will adjust the flow of gas through the passageway of the duct, decreasing the flow. In addition, with the interior volume of the plenum being defined between the first wall of the plenum that supports the gas flow regulator ducts and the second wall of the plenum that is positioned on the opposite side of the plenum interior volume from the first wall, moving each regulator duct axially so that the second end of the duct is spaced further away from the second wall of the plenum will increase the area between the duct second end and the plenum second wall and enhance the free flow of gas supplied through the plenum interior volume to the duct and through the duct passageway into the test chamber interior volume. Conversely, moving each duct axially through the hole of the plenum first wall toward the second wall of the plenum so that the duct second end is positioned closer to the plenum second wall decreases the area between the duct second end and the plenum second wall and restricts the free flow of gas supplied through the plenum to the duct and through the duct passageway into the test chamber interior volume.

Thus, by rotating each duct in its hole of the plenum first wall and by axially adjusting the position of each duct in its hole in the plenum first wall the rate of gas flow through each duct passageway from the plenum interior volume to the test chamber interior volume can be adjusted. When the desired rate of gas flow through each duct passageway is achieved, the duct can be held in its adjusted position by tightening the screw of the locking mechanism, thereby holding the duct stationery in its adjusted position relative to the plenum wall.

By providing a plurality of holes in the plenum first walls on the opposite sides of the test chamber interior volume and a plurality of gas flow regulators of the invention mounted in the holes, the flow of gas from the plenum interior volume into different portions of the test chamber interior volume can be adjusted, thereby achieving a means of obtaining a more spatially uniform rate of temperature change throughout various test specimens or throughout various portions of a test specimen positioned in the interior volume of the test chamber.

BRIEF DESCRIPTION OF THE DRAWING FIGURES

Further features of the invention are set forth in the following detailed description of the preferred embodiment of the invention and in the following drawing figures wherein.

DETAILED DESCRIPTION OF THE INVENTION

Figure 1:
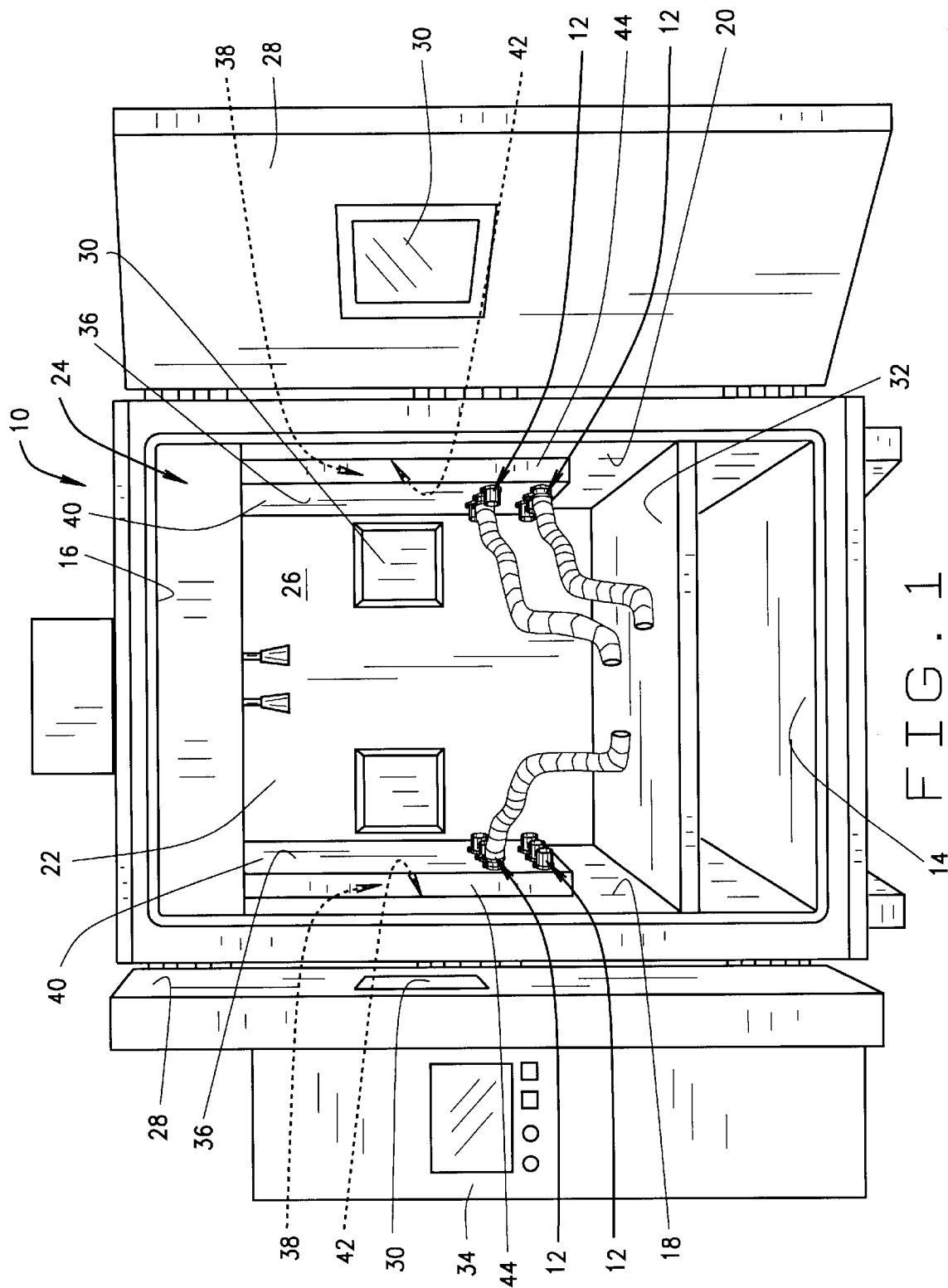
FIG. 1 is a front elevation view of a typical thermodynamic environmental testing chamber employing the gas flow regulators of the invention.

FIG. 1 shows a front elevation view of the operative environment of a thermodynamic environmental testing chamber with which the gas flow regulator of the invention may be employed. However, it should be understood that the operative environment shown in FIG. 1 and to be described is not intended to limit the gas flow regulator of the invention with use only in the environment of the testing chamber. The simplistic construction of the gas flow regulator may be employed in a variety of other environments where it is desired to provide a means of controlling or regulating the flow of a fluid from a volume on one side of a dividing wall to another volume on the opposite side of the dividing wall by means of an inexpensively manufactured and installed and an easily operated control device.

The construction of the thermodynamic environmental testing chamber 10 shown in FIG. 1 is, for the most part, conventional apart from the presence of the novel gas flow regulator 12 of the invention. Therefore, the testing chamber 10 will be described in only general detail.

As seen in FIG. 1, the thermodynamic environmental testing chamber 10 is basically comprised of a large box-shaped housing having a bottom wall structure 14 and an opposite top wall structure 16, a left side wall structure 18 and an opposite right side wall structure 20 as viewed in FIG. 1, a back wall structure 22 and a front opening 24 providing access into a first volume 26 of the test chamber interior. One or more doors 28 are connected to the front of the chamber 10 and close over the front opening 24 to seal closed the chamber interior volume 26. The wall structures and the doors are typically thermally insulated. A plurality of viewing windows 30 are often provided in the doors and one or more of the chamber wall structures. A specimen platform 32 is provided in the chamber interior 26 for supporting one or more specimens to be tested. Heating or cooling of test specimens placed in the chamber interior 26 and supported on the platform 32 is provided by supplying heated or cooled gas to the chamber interior in a manner to be explained.

The temperature of the gas and its rate of flow supplied into the test chamber interior 26 is controlled by an electronic control module 34. Control modules 34 are typically interfaced with heating, cooling and blower systems (not shown) of the testing chamber 10 for controlling such systems to achieve the desired testing environment in the interior volume 26 of the test chamber.

The typical test chamber 10 employs a plenum to direct the flow of gas generated by the test chamber to opposite sides of the chamber interior volume 26. In the example shown in FIG. 1, the test chamber plenum is comprised of two sections 36 that extend downwardly across the opposite left side wall structure 18 and right side wall structure 20 in the interior volume 26 of the test chamber. Each of these plenum sections 36 encloses a second volume 38 that is supplied with a gas flow from the gas flow source (not shown) and directs the flow of gas through the interior volume of the plenum downwardly across the opposite sides of the chamber interior volume. Each plenum section 36 is basically comprised of a first wall 40 that is spaced by the second volume 38 in the interior of the plenum from a second wall 42 of the air plenum section that could be a portion of the test chamber left and right side wall structures 18, 20 or could be a separate wall from the side wall structures. As seen in FIG. 1, peripheral walls 44 space the first plenum wall 40 from the second plenum wall 42 and enclose the second interior volume 38 of the plenum. With the plenum sections 36 positioned against the opposite left and right side wall structures 18, 20 of the test chamber as shown in FIG. 1, the first plenum walls 40 separate the first volume 26 of the test chamber interior from the second volume 38 of the plenum interiors. The plenum first walls 40 are provided with one or more, and preferably a plurality of, port openings or holes 46 that provide communication between the first volume 26 of the chamber interior and the second volume 38 of the plenum interior. The holes 46 channel the flow of gas through the plenum second volume 38 through the holes to the first volume 26 of the chamber interior.

The gas flow regulator 12 of the invention is used in the thermodynamic environmental testing chamber 10 described above in its preferred operative environment. However, as explained earlier, the gas flow regulator 12 of the invention may be employed in regulating the flow of gas from a second volume on one side of a wall to a first volume on the opposite side of the wall. The simplistic construction of the gas flow regulator 12 as shown in FIG. 2 is comprised of a duct member 48 and a locking mechanism 50.

The duct member 48 may be constructed of metal or plastic resins that are capable of withstanding the changes in temperature to which the duct will be subjected in use in the testing chamber. The duct 48 has a length between opposite first 52 and second 54 ends of the duct. The length of the duct between its opposite ends can be varied, depending on how far it is desired that the duct reach into the testing chamber interior volume 26 from the air plenum 36 as will be explained. A cylindrical interior surface 56 of the duct defines a passageway through the duct between its opposite ends. The interior surface 56 and the passageway it defines have a center axis 58 extending through the duct. The duct exterior surface 60 is also cylindrical and has a circumferential dimension or an exterior diameter dimension that matches the interior circumferential dimension or interior diameter dimension of a hole 46 or channeling port in the plenum first wall 40. This dimensioning of the duct exterior surface enables it to be inserted into one of the holes 46 in the plenum first wall 40 in a tight friction fit. The tight fit of the duct 48 in the plenum hole 46 minimizes the leakage of the flow of gas from the plenum second volume 38 through the connection of the plenum hole inner edge 62 with the duct exterior surface while still allowing the duct 48 to slide within the hole 46 while the edge of the plenum first wall surrounding the hole provides support for the duct. In the preferred embodiment of the flow regulator, the duct first end 52 has a circular or annular edge 64 that lies in a plane perpendicular to the duct center axis 58. In alternative embodiments, the shape of the duct first end 52 can be varied as desired for the purpose of directing gas flow from the duct first end or for other purposes. The opposite, second duct end 54 is beveled in shape. Preferably, the duct second end 54 has an elliptically shaped edge 66 that lies in a plane that is oriented obliquely to the duct center axis 58. The beveled shape of the duct second end 54 forms the second end with a shroud projection 68 that projects out over the opening 70 of the duct passageway at the duct second end 54 as viewed in FIG. 2. The beveled shape of the duct second end 54 also gives the second end an exposed opening 70 to the duct passageway that faces away from the projecting shroud 68.

Figure 2:
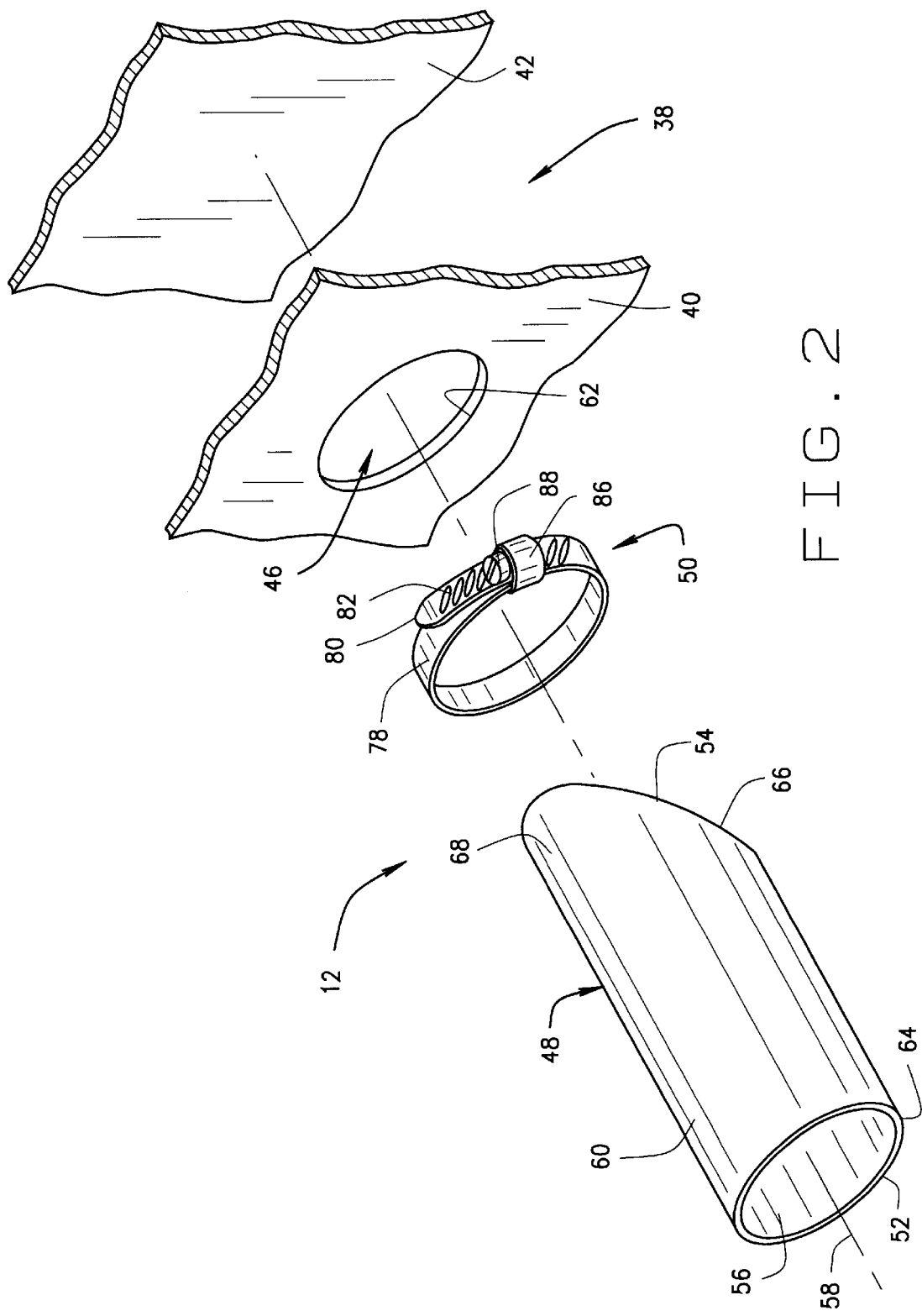
FIG. 2 is an assembly view of the gas flow regulator of the invention illustrating its assembly to a plenum of the test chamber of FIG. 1.
Figure 4:
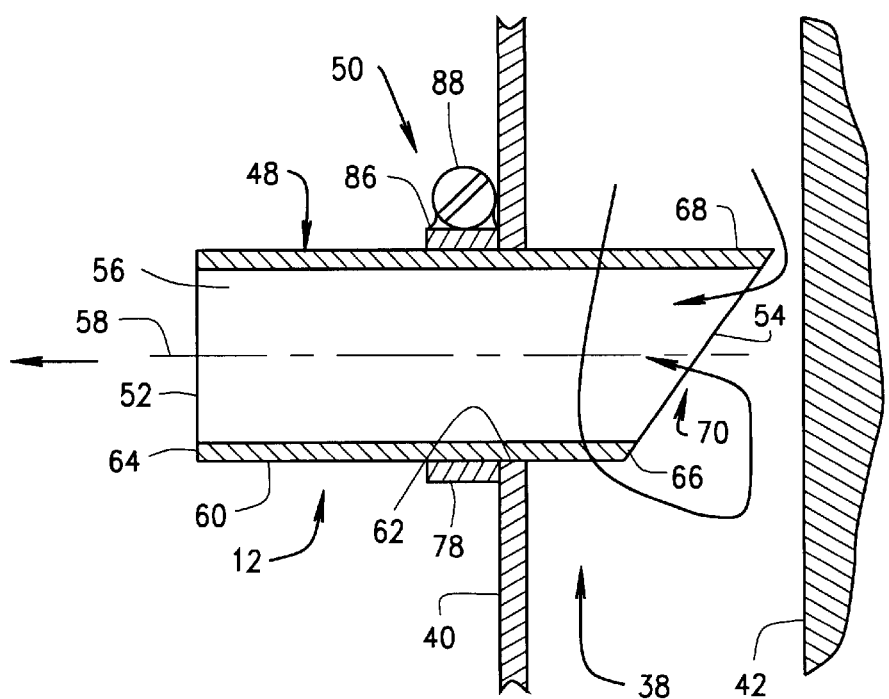
FIG. 4 is a partial, cross-section view similar to that of FIG. 3 but showing the gas flow regulator in another adjusted position of the regulator relative to the plenum.
Figure 3:
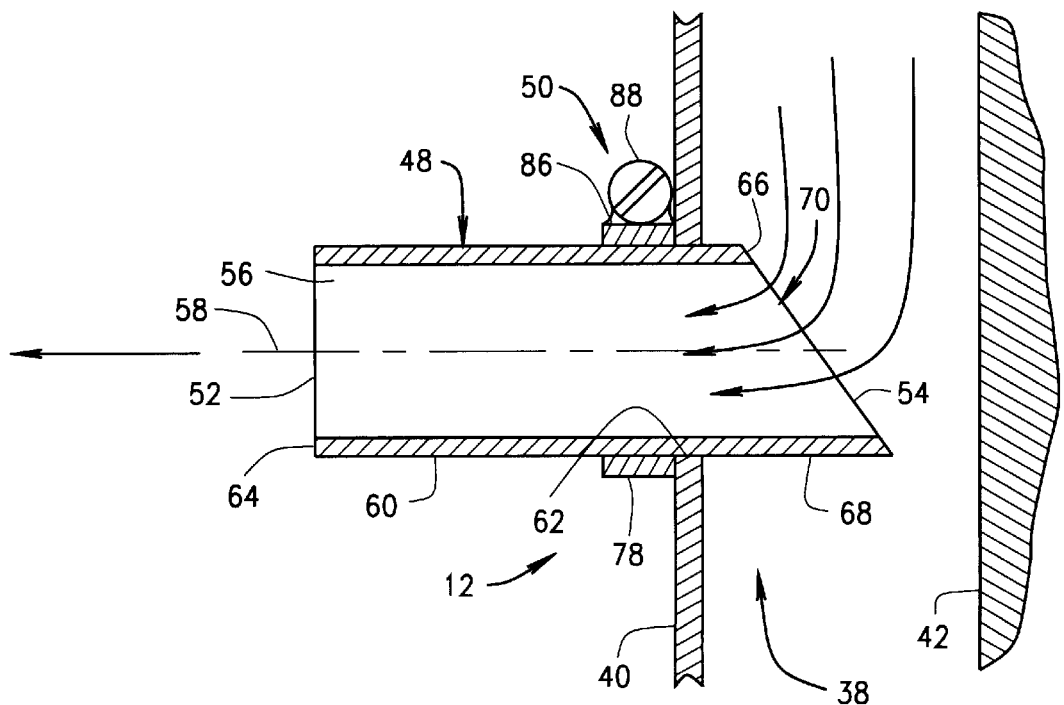
FIG. 3 is a partial, cross-section view of the gas flow regulator of the invention assembled to the plenum of the test chamber of FIG. 1.

The gas flow regulator 12 is assembled to the test chamber 10 as shown in FIGS. 2 through 4. A regulator duct 48 is positioned in each of the holes 46 in the test chamber plenum first wall 40 by sliding the duct from the first volume 26 of the chamber interior through the hole 46 into the second volume 38 of the plenum interior. The duct is positioned in the hole with the duct first end 52 positioned in the first volume 26 of the test chamber interior and with the duct second end 54 positioned in the second volume 38 of the plenum interior volume as shown in FIGS. 2 through 4. With the tight friction fit of the hole interior edge 62 around the exterior surface 60 of the duct, the plenum first wall 40 supports the duct in the hole with the duct center axis 58 substantially perpendicular to the plenum first wall 40.

The locking mechanism 50 of the gas flow regulator is preferably an adjustable band clamp of the type known in the prior art. As in a typical band clamp and as shown in FIG. 2, the band 78 of the band clamp has opposite first 80 and second 82 ends with slots 84 formed into the first end of the band that function as rack teeth. A screw housing 86 containing an adjustment screw 88 is provided at the opposite, second end 82 of the band. The band first end 80 is inserted into the screw housing 86 forming the band in a loop, and on rotation of the adjustment screw 88 in the screw housing 86, the threads of the screw pass through the slots 84 of the band first end adjusting the size of the loop formed by the band.

The band 78 of the locking mechanism is positioned over the duct exterior surface 60 in the first volume 26 of the test chamber interior when the duct is assembled to the plenum first wall 40, where the locking mechanism 50 is accessible from the test chamber interior. The screw housing 82 of the locking mechanism is secured to the plenum first wall 40 by a spot weld or other equivalent means to hold the locking mechanism stationary relative to the first wall. With the loop formed by the band 78 expanded, the duct 48 is still free to move axially through the plenum first wall hole 46 and rotationally in the hole. By screwing the adjustment screw 88 in the screw housing 86 of the locking mechanism, the band 78 can be constricted around the duct exterior surface 60 and thereby the locking mechanism holds the duct in a stationary position relative to the first wall 40 of the plenum.

In the illustrative environment of the invention, a gas flow regulator 12 is positioned in each of the holes 46 in the first walls 40 of the plenum sections 36 on opposite sides of the first volume 26 of the test chamber to regulate the flow of gas through the plenum second volume 38 to the first volume 26 of the test chamber interior.

In operation of the test chamber 10 employing the flow regulators 12 of the invention, with a flow regulator 12 positioned in each of the holes 46 of the plenum first walls 40, the test chamber is activated causing a flow of gas (either heated or cooled) through the second volume 38 of the plenum interior. In the illustrative embodiment shown, the flow of gas is directed downwardly through the second volume 38 of the plenum interior toward the holes 46 adjacent the bottom of the plenum sections 36. The duct 48 of each of the gas flow regulators 12 positioned in each of the plenum holes 46 channels the flow of gas from the plenum second volume 38, through the duct passageway and into the interior volume 26 of the test chamber.

With the duct second end 54 having a beveled edge 66, rotating the duct in the plenum first wall 40 so that the exposed elliptical opening 60 of the beveled edge faces into the downwardly directed flow of gas through the plenum interior volume 38 as shown in FIG. 3 will result in a greater amount of gas being channeled through the passageway of the duct and into the test chamber interior volume 26. This is due to the ramming effect of the flow of gas downwardly through the plenum interior 38 into the exposed elliptical opening 70 of the duct. By gradually rotating the duct 48 in the plenum first wall hole 46 so that the exposed opening 70 is gradually directed away from the flow of gas channeled downwardly through the plenum, the ram effect of the flow of gas on the exposed opening 70 is decreased and the flow of gas through the duct is also decreased. Turning the duct 180 degrees in the plenum wall hole to its position shown in FIG. 4 where the elliptical opening 70 of the beveled edge faces away from the flow of gas will negate the ramming effect of the flow of gas on the exposed opening 70 and will decrease the flow of gas through the duct passageway.

In addition to adjusting the flow of gas through the duct 48 by rotating the duct in the hole 46 of the plenum first wall 40, moving each regulator duct 48 axially so that its second end 54 is spaced further away from the second wall 42 of the plenum will increase the area between the duct second end 54 and the plenum second wall 42 and enhance the free flow of gas supplied through the second volume 38 of the plenum to the duct and through the duct passageway into the first volume 26 of the test chamber. Conversely, moving each duct 48 axially through the plenum first wall holes 46 toward the plenum second wall 42 so that the duct second end 54 is positioned closer to the plenum second wall 42 decreases the area between the duct second end 54 and the plenum second wall 42 and restricts the free flow of gas supplied through the second volume 38 of the plenum to the duct and through the duct passageway into the test chamber interior volume 26. Thus, by rotating each duct 48 in its hole 46 of the first walls 40 of the plenum sections and by axially adjusting the position of each duct 48 in its hole 46 in the plenum first walls, the rate of gas flow through each duct passageway from the second volume 38 of the plenum to the first volume 26 of the test chamber can be adjusted. When the desired rate of gas flow through each duct passageway is achieved, the duct 48 can be held in its adjusted position by tightening the screw 88 of the locking mechanism 50, thereby holding the duct stationary in its adjusted position relative to the plenum first wall 40.

By providing a plurality of holes 46 in the plenum first walls 40 on the opposite sides of the test chamber interior volume 26 and a plurality of gas regulators 12 mounted in the holes, the flow of gas from the plenum interior volume 38 into different portions of the test chamber interior volume 26 can be adjusted, thereby achieving a means of obtaining a more spatially uniform rate of temperature range throughout various test specimens or throughout various portions of a test specimen positioned in the interior volume of the test chamber.

While the present invention has been described by reference to a specific embodiment, it should be understood that modifications and variations of the invention may be constructed without departing form the scope of the invention defined in the following claims. For example, each of the flow regulator ducts could be mounted stationary in the plenum wall and be provided with a beveled second end that is mounted on the duct for relative rotational and axial movement of the second end relative to the stationary duct, the gas regulator ducts could be mounted in a tight friction fit in the plenum wall holes without the need for a locking mechanism, and the flow regulator ducts could be provided with flexible hose similar to those employed in the prior art directing the flow of gas from the regulators to a particular location in the test chamber interior.

What is claimed:

1. A gas flow regulator for controlling a flow of gas between first and second volumes separated by a wall having at least one hole through the wall, the gas flow regulator comprising:

a duct having a length with opposite first and second ends, the duct having an interior passageway with a center axis that extends between the duct first and second ends, the duct is mountable in the one hole of the wall with the duct first end in the first volume and the duct second end in the second volume and whereby the duct can be axially adjustably positioned in the one hole relative to the wall, and the duct second end being beveled relative to the duct axis.

2. The gas flow regulator of claim 1, wherein:

at least one end of the duct is rotatable about the axis.

3. The gas flow regulator of claim 1, wherein:

the duct is cylindrical.

4. The gas flow regulator of claim 1, wherein:

the duct exterior surface is adapted to be mounted in the one hole of the wall whereby the duct can be rotated about the axis.

5. The gas flow regulator of claim 1, wherein:

a locking mechanism is positioned on the duct exterior surface and is operable to selectively lock the duct in a stationary position relative to the wall.

6. The gas flow regulator of claim 1, wherein:

the duct first end is positioned in a plane that is oriented perpendicularly to the axis.

7. An apparatus for controlling conditions in a testing environment, the apparatus comprising:

a test chamber having an interior first volume, a first wall enclosing at least a portion of the first volume and separating the first volume from a second volume on an opposite side of the first wall from the first volume, a second wall spaced from the first wall by the second volume, and at least one hole through the first wall;

a duct having a length with opposite first and second ends, the duct having an interior passageway with a center axis extending between the first and second ends of the duct and an exterior surface, the duct being mounted in the hole of the first wall for axially adjusting movement of at least one of the first and second ends relative to the first wall, and the duct second end is beveled relative to the duct axis.

8. The apparatus of claim 7, wherein:

the at least one hole through the first wall is one of a plurality of holes through the first wall and the duct is one of a plurality of like ducts mounted in the plurality of holes.

9. The apparatus of claim 7, wherein:

the first wall is one pair of like first walls positioned on opposite sides of the first volume.

10. The apparatus of claim 7, wherein:

the duct is also rotatable relative to the first wall.

11. The apparatus of claim 7, wherein:

the duct is mounted in the one hole of the first wall with the duct first end in the first volume and the duct second end in the second volume and the duct is mounted for axially adjusting movement of the duct in the one hole relative to the first wall.

12. The apparatus of claim 7, wherein:

the duct is cylindrical.

13. The apparatus of claim 7, wherein:

the duct is mounted in the one hole also for rotation of the duct in the one hole relative to the first wall.

14. The apparatus of claim 7, wherein:

the duct is mounted in the one hole of the first wall for axially adjusting movement of the duct whereby the duct second end can be moved axially into contact with the second wall.

15. The apparatus of claim 7, wherein:

a locking mechanism is positioned on the duct and is operable to lock the duct in a stationary position relative to the first wall.

16. The apparatus of claim 7, wherein:

the first wall is one of a pair of first walls positioned on opposite sides of the first volume, the one hole is one of a plurality of holes in the pair of first walls, and the duct is one of a plurality of like ducts mounted in the plurality of holes.

17. The apparatus of claim 16, wherein:

a source of gas flow communicates with the second volume and supplies a flow of gas that is channeled through the second volume and through the plurality of ducts into the first volume.

\* \* \* \* \*